United States Patent [19]
Miyata et al.

[11] Patent Number: 5,895,564
[45] Date of Patent: Apr. 20, 1999

[54] METHOD AND A DEVICE FOR CONTROLLING AN AIR/FUEL RATIO SENSOR

[75] Inventors: Shigeru Miyata; Noriaki Kondo; Hiroshi Inagaki, all of Nagoya, Japan

[73] Assignee: NGK Spark Plug Co., Ltd., Aichi, Japan

[21] Appl. No.: 08/927,527

[22] Filed: Sep. 11, 1997

[30] Foreign Application Priority Data

Sep. 30, 1996 [JP] Japan ................... 8-280331

[51] Int. Cl.$^6$ ..................... G01N 27/407
[52] U.S. Cl. ............... 205/784.5; 204/425; 204/426; 205/785
[58] Field of Search ............... 204/421–429; 205/783.5, 784, 784.5, 785

[56] References Cited

U.S. PATENT DOCUMENTS 4,365,604  12/1982  Sobe ..................... 204/425

FOREIGN PATENT DOCUMENTS

| 62-76446 | 4/1987 | Japan. |
| 62076452 A | 4/1987 | Japan. |
| 62-190461 | 8/1987 | Japan. |
| 62190461 A | 8/1987 | Japan. |
| 5-80619 | 11/1993 | Japan. |
| 7-89109 | 9/1995 | Japan. |

*Primary Examiner*—T. Tung
*Attorney, Agent, or Firm*—Sughrue, Mion, Zinn, Macpeak & Seas, PLLC

[57] ABSTRACT

An air/fuel ratio sensor is controlled such that the oxygen concentration of the measurement gas can be detected from a pump current substantially instantaneously after a heater turns on. In the air/fuel ratio sensor an oxygen pumping cell and an oxygen concentration measuring cell are each formed of a solid electrolytic layer interposed between a pair of porous electrodes. One of the electrodes of each cell defines a measurement gas chamber in which the diffusion of the measurement gas is controlled. After a micro current is supplied to the other electrode of the oxygen concentration measuring cell for a predetermined period of time, thereby forming an internal reference oxygen source, the supply of the micro current is stopped and at the same time a pump current in the oxygen pumping cell starts to be controlled until the interelectrode voltage of the oxygen concentration measuring cell reaches a target voltage. After the air/fuel ratio sensor is activated, the supply of the micro current is restarted.

8 Claims, 5 Drawing Sheets

METHOD AND A DEVICE FOR CONTROLLING AN AIR/FUEL RATIO SENSOR

BACKGROUND OF THE INVENTION

This invention relates to a method and a device for controlling or quickly activating an air/fuel ratio sensor provided with an oxygen pumping cell and an oxygen concentration measuring cell. The cells are each composed of a pair of porous electrodes formed on the respective side faces of a solid electrolytic layer conductive of oxygen ion.

Conventionally, it is proposed, for example, in the laid-open Japanese patent application Nos. 62-76446 and 62-190461 that an air/fuel ratio sensor composed of an oxygen pumping cell and an oxygen concentration measuring cell is provided for detecting the combustion condition or air/fuel ratio of an engine or any other combustion device from the oxygen concentration in the gas exhausted from the combustion device. The oxygen pumping cell and the oxygen concentration measuring cell each is formed of a solid electrolytic layer of zirconia or other material conductive of oxygen ion, sandwiched by a pair of porous electrodes of platinum or other. Each cell is disposed such that one electrode of each cell is in contact with a measurement gas chamber communicating via a diffusion controlled layer with the gas to be measured. The other electrode of the oxygen concentration measuring cell opposite to the measurement gas chamber is closed, and part of the oxygen in the closed space can leak via a leakage resisting part to the outside.

In the conventional air/fuel ratio sensor, a micro current is supplied to the oxygen concentration measuring cell in the direction in which oxygen is pumped from the measurement gas chamber to the closed space, which is caused to function as an internal reference oxygen source. A detection voltage is generated between the porous electrodes of the oxygen concentration measuring cell, corresponding to the ratio of the partial pressure of oxygen in the internal reference oxygen source and the partial pressure of oxygen in the measurement gas chamber. The pump current supplied to the oxygen pumping cell is controlled, such that the detection voltage reaches a predetermined target voltage or the concentration of oxygen in the measurement gas chamber reaches a predetermined concentration. The concentration of oxygen in the gas to be measured is detected by detecting the controlled pump current.

The conventional air/fuel ratio sensor is also provided with a separate heater for heating the oxygen concentration measurement cell and the oxygen pumping cell to a predetermined activation temperature of about 650° C. or higher, because each cell must be sufficiently heated and activated for the purpose of precisely detecting the oxygen concentration.

Figure 5:
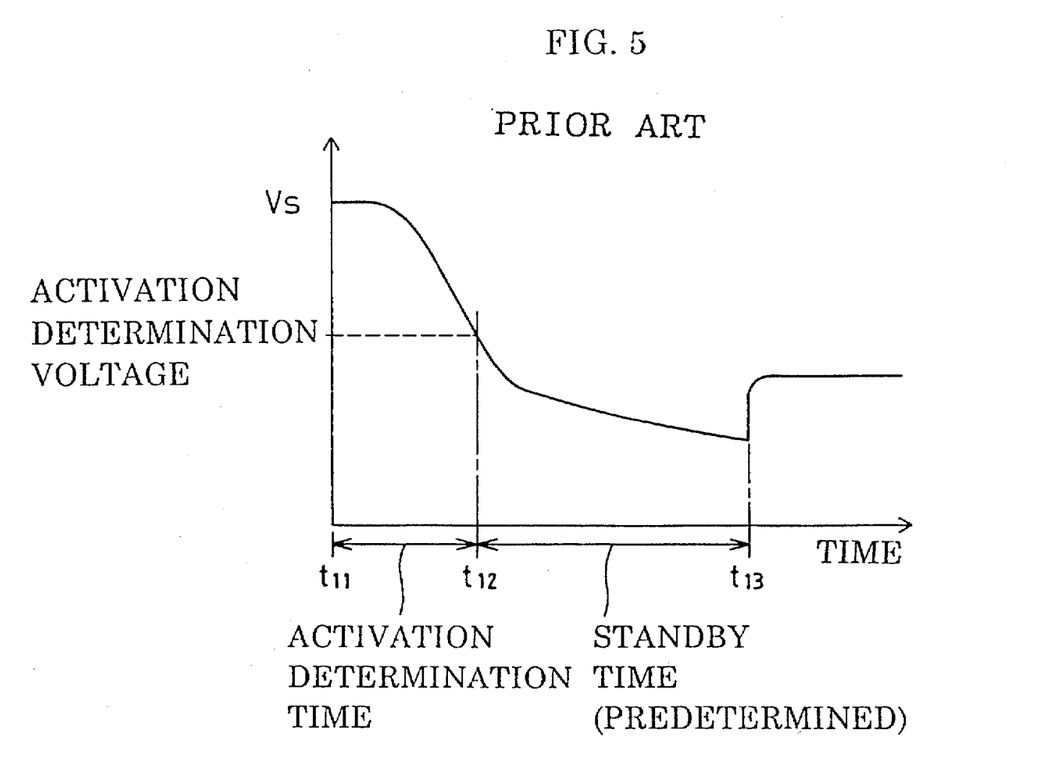
FIG. 5 is a time chart explaining the conventional process of determining the activation of the sensor.

In operation of the conventional air/fuel ratio sensor, as shown in FIG. 5, at time t11 when the heater is turned on, a micro current is supplied to the oxygen concentration measuring cell for preparing the internal reference oxygen source. Subsequently, at time t12 when the interelectrode voltage of the oxygen concentration measuring cell lowers to a predetermined activation determination voltage, the oxygen concentration measuring cell is substantially activated. After a predetermined period of standby time elapses, then at time t13 that each cell can be completely activated and the control over a pump current is started. The oxygen concentration measuring cell and the oxygen pumping cell are thus controlled.

Conventionally before the activation of the air/fuel ratio sensor, the micro current is supplied to the oxygen concentration measuring cell at the same time the heater is turned on, and the generated interelectrode voltage of the oxygen concentration measuring cell is detected. Accordingly, the internal resistance of the oxygen concentration measuring cell, which decreases as temperature rises, is measured. The air/fuel ratio sensor is activated only by a detection of the interelectrode voltage, however, the following two problems result.

① Since the interelectrode voltage varies with the internal resistance of the oxygen concentration measuring cell and with the concentration of oxygen in the measurement gas, even if the interelectrode voltage decreases down to the activation determination voltage, it cannot be precisely determined whether or not the temperature of the oxygen concentration measuring cell reaches a desired temperature.

② If the control over the pump current is started when the oxygen concentration measuring cell is insufficiently activated, the interelectrode voltage of the oxygen concentration measuring cell is large because of a drop in the voltage equaling the micro current multiplied by the internal resistance of the oxygen concentration measuring cell. The pump current becomes incorrectly controlled.

To solve the aforementioned problems and to precisely detect the oxygen concentration in the measurement gas, in the conventional method, the air/fuel ratio sensor is activated after a predetermined period of standby time elapses after the interelectrode voltage lowers down to the activation determination voltage. Specifically, after the oxygen concentration measuring cell is sufficiently activated to such degree that the internal resistance of the oxygen concentration measuring cell can be ignored, the oxygen concentration measuring cell and the oxygen pumping cell are determined to be activated, the pump current starts to be supplied to the oxygen pumping cell under control, and the oxygen concentration is detected.

In the aforementioned conventional control method, the pump current can be controlled without being affected by the internal resistance of the oxygen concentration measuring cell. Although the incorrect control of the pump current or the blackening of the oxygen pumping cell can be avoided, much time is required until the oxygen concentration can be detected. Because, a period of time is required for determining the activation of each cell from when the heater is turned on until the interelectrode voltage of the oxygen concentration measuring cell decreases to the activation determination voltage. After the predetermined period of standby time further elapses, each cell is activated, the control over the pump current is started, and the oxygen concentration is detected. It follows that the oxygen concentration cannot be detected, until each cell is substantially sufficiently activated.

SUMMARY OF THE INVENTION

Wherefore, an object of the present invention is to provide an oxygen concentration control method which requires only a minimum period of time from when a heater is energized till the oxygen concentration in the measurement gas starts to be detected.

Another object of the invention is to provide an oxygen concentration control device which requires only a minimum period of time from when a heater is energized till the oxygen concentration in the measurement gas starts to be detected.

To attain these or other objects, the present invention provides a method of controlling an air/fuel ratio sensor. The air/fuel ratio sensor has a sensor body composed of an oxygen pumping cell and an oxygen concentration measuring cell. Both of the oxygen pumping cell and the oxygen concentration measuring cell are provided with a solid electrolytic conductive layer of oxygen ion interposed between a pair of porous electrodes. A measurement gas chamber is defined by one electrode of each cell and communicates via a diffusion controlled layer with the gas to be measured. The other electrode of the oxygen concentration measuring cell opposite to the measurement gas chamber forms a closed space. Part of the oxygen in the closed space can leak via a leakage resisting part to the outside. The air/fuel ratio sensor is further provided with a heater for heating and activating the heater body, a heater energizing unit for supplying electricity to the heater and heating the air/fuel ratio sensor, and a micro current supply unit for supplying a micro current to the oxygen concentration measuring cell in the direction in which the oxygen in the measurement gas chamber is pumped into the closed space, causing the closed space to function as an internal reference air/fuel ratio sensor. The air/fuel ratio sensor is also provided with a measuring unit for measuring the interelectrode voltage of the oxygen concentration measuring cell, and a pump current controller for supplying pump current to the oxygen pumping cell. The concentration of oxygen in the gas to be measured can be detected by the air/fuel ratio sensor from the pump current controlled by the pump current controller and the interelectrode voltage of the oxygen concentration measuring cell measured by the measuring unit. The air/fuel ratio sensor is controlled such that the oxygen concentration can be detected quickly after the heater energizing unit turns on the heater. The heater energizing unit turns on the heater at the same time the micro current supply unit starts supplying a micro current to the oxygen concentration measuring cell, thereby causing the closed space to function as the internal reference oxygen source. Subsequently, after a predetermined period of time elapses, the micro current supply unit is stopped from supplying the micro current to the oxygen concentration measuring cell and at the same time the pump current controller starts controlling the pump current.

In the method of controlling the air/fuel ratio sensor, after the pump current is controlled, the sensor body is determined to be activated when the interelectrode voltage of the oxygen concentration measuring cell reaches a predetermined voltage.

Also, regarding the method of controlling the air/fuel ratio sensor, when the sensor body is activated, the micro current supply unit resumes the supply of the micro current to the oxygen concentration measuring cell.

The present invention also provides a device for controlling the air/fuel ratio sensor such that the oxygen concentration can be detected quickly after the heater energizing unit turns on the heater. The control device is comprised of a micro current supply start unit for starting the heater energizing unit supplying electricity to the heater and at the same time operating the micro current supply unit to supply a micro current to the oxygen concentration measuring cell, causing the closed space to function as the internal reference oxygen source. The control device is also comprised of a timer for setting a predetermined period of time after the micro current supply start unit operates the micro current supply unit, and a supply stop unit for stopping the supply of the micro current after the micro current supply unit supplies the micro current to the oxygen concentration measuring cell for the predetermined period of time. The control device further comprises a pump current control start unit for starting the pump current controller controlling the pump current concurrently with the stop of micro current supply.

The device for controlling the air/fuel ratio sensor has an activation determination unit for determining whether or not the pump current controller can control the interelectrode voltage of the oxygen concentration measuring cell to be a predetermined target voltage after the pump current control start unit starts the pump current controller, and determining that the sensor body is activated when the interelectrode voltage reaches the predetermined target voltage.

The device for controlling the air/fuel ratio sensor also has a micro current supply resuming unit for restarting the micro current supply unit which supplies micro current to the oxygen concentration measuring cell when the activation determination unit determines that the sensor body is activated.

In the aforementioned method of controlling the air/fuel ratio sensor, first the heater is turned on at the same time a micro current starts to be supplied to the oxygen concentration measuring cell, causing the closed space of the electrode of the oxygen concentration measuring cell opposite to the electrode defining the measurement gas chamber to function as the internal reference oxygen source. Subsequently, after a predetermined period of time elapses, the supply of micro current to the oxygen concentration measuring cell is stopped and at the same time the pump current starts to be controlled. When the interelectrode voltage of the oxygen concentration measuring cell is adjusted to the target voltage by controlling the pump current, the sensor body is activated.

In the conventional control method, a micro current is supplied to the oxygen concentration measuring cell and the interelectrode voltage or internal resistance of the oxygen concentration measuring cell is detected. The oxygen concentration measuring cell and the oxygen pumping cell are activated based on the detected interelectrode voltage. Subsequently, the pump current starts to be controlled.

Different from the conventional method, in the invention, after micro current is supplied to the oxygen concentration measuring cell for a predetermined period of time, causing the closed space of the electrode of the oxygen concentration measuring cell opposite to the electrode defining the measurement gas chamber to function as the internal reference oxygen source, the supply of the micro current is stopped and the pump current control is started.

In the control method according to the invention, since the supply of micro current to the oxygen concentration measuring cell is stopped when the pump current control is started, the interelectrode voltage of the oxygen concentration measuring cell corresponds to the ratio of the reference oxygen partial pressure of the closed space and the oxygen partial pressure in the measurement gas chamber and is not affected by the internal resistance of the oxygen concentration measuring cell.

Even if the sensor body is not activated when the pump current control is started, the interelectrode voltage of the oxygen concentration measuring cell is not increased by the influence of the internal resistance. Therefore, the pump current can be used for detecting the concentration of the oxygen in the measurement gas.

Additionally, when the sensor body is not activated, even if the pump current is controlled using a deviation in the voltages, it is difficult to control the interelectrode voltage of the oxygen concentration measuring cell to reach the target voltage. However, while the temperature of the sensor body is raised by supplying electricity to the heater, the interelectrode voltage of the oxygen concentration measuring cell can approach the target voltage.

In the present invention, the sensor body is activated when the interelectrode voltage of the oxygen concentration measuring cell reaches the target voltage by the control of the pump current.

Therefore, as soon as the pump current is controlled such that the interelectrode voltage of the oxygen concentration measuring cell reaches the target voltage after the heater is turned on, the sensor body is activated. Different from the conventional method, the time required to determine activation is not excessively long.

In the present invention, the micro current is supplied to the oxygen concentration measuring cell for preparing the internal reference oxygen source only for a predetermined period of time after the heater turns on. When the pump current starts to be controlled after the predetermined period of time, the pump current can be controlled without being affected by the internal resistance of the oxygen concentration measuring cell which was operated before the sensor body is activated. The internal resistance can be sufficiently reduced by increasing the temperature of the sensor body to the desired activation temperature of, for example, 650° C. and activating the sensor body. Therefore, the pump current can be controlled without being affected by the internal resistance of the oxygen concentration measuring cell. After the sensor body is activated, the micro current supply unit may restart supplying micro current to the oxygen concentration measuring cell.

In the present invention, after the micro current is supplied to the oxygen concentration measuring cell for the predetermined period of time, the supply of micro current to the oxygen concentration measuring cell is stopped at least from when the pump current is controlled till the sensor body is determined to be activated. While the micro current is stopped, the concentration of oxygen in the closed space of the oxygen concentration measuring cell must not deviate from the reference oxygen concentration because of oxygen leakage via the leakage resisting part to the outside.

However, the oxygen accumulated in the closed space by supplying micro current to the oxygen concentration measuring cell does not leak instantly. The oxygen in the closed space can maintain its reference concentration for a short period of time. The inventors conducted experiments on the air/fuel ratio sensor embodying the invention and confirmed that the reference oxygen concentration can be kept for 10 seconds or longer.

The activation of the sensor body can be precisely determined from the interelectrode voltage of the oxygen concentration measuring cell under control of the pump current, by conducting experiments and setting the predetermined period of time for which micro current is supplied to the oxygen concentration measuring cell after the heater turns on, such that the reference oxygen concentration in the closed space can be maintained from a time when the micro current supply is stopped till the sensor body activation.

In some designs of the sensor body, the reference oxygen concentration can be maintained in the closed space only for a short time and the reference oxygen concentration in the closed space cannot be secured until the sensor body is activated. To solve the problem, first the micro current is supplied to the oxygen concentration measuring cell, the control over pump current is started, and then the micro current is periodically supplied to the oxygen concentration measuring cell. In this manner, when the micro current is periodically supplied to the oxygen concentration measuring cell, even after the control over pump current is started for the determination of activation, the concentration of oxygen in the closed space can be held as a reference. Therefore, the activation of the sensor body can be precisely determined from the interelectrode voltage of the oxygen concentration measuring cell while the pump current is controlled.

In this case, however, the pump current control needs to be discontinued when micro current is supplied to the oxygen concentration measuring cell. Specifically, if the pump current is controlled while the micro current is supplied to the oxygen concentration measuring cell, the pump current will increase by influence of the internal resistance of the oxygen concentration measuring cell. As a result, the pump current is incorrectly controlled, or blackening is generated in the oxygen pumping cell Therefore, when micro current is periodically supplied to the oxygen concentration measuring cell after the pump current control is started, so the closed space functions as the internal reference oxygen source, the pump current control can be discontinued while the micro current is supplied.

Even if the sensor body is insufficiently activated while the pump current is controlled, the output of pump current can be used for detecting the concentration of oxygen in the measurement gas. In this case, the air/fuel ratio cannot be precisely detected because the oxygen pumping cell is not activated sufficiently. Therefore, the air/fuel ratio needs to be controlled in the control mode different from the usual mode.

The present invention provides a device for controlling the air/fuel ratio sensor in the aforementioned method. In the device, the heater energizing unit starts supplying electricity to the heater, the micro current supply start unit operates the micro current supply unit to supply micro current to the oxygen concentration measuring cell, causing the closed space to function as the internal reference oxygen source, and the timer counts a predetermined period of time. Subsequently, after the predetermined period of time elapses, the supply stop unit stops the micro current supply unit from supplying micro current to the oxygen concentration measuring cell and at the same time the pump current control start unit starts the pump current controller controlling pump current.

Further in the control device the activation determination unit determines whether or not the interelectrode voltage of the oxygen concentration measuring cell is controlled by the pump current controller to reach the target voltage. When the interelectrode voltage reaches the target voltage, the sensor body is activated.

Therefore, in the control device, after the heater turns on, the pump current control is instantly started, and the controlled pump current can be used for detecting the concentration of oxygen in the measurement gas. Additionally, in the control device, after the heater turns on, it can be instantly determined that the sensor body is prepared to detect the oxygen concentration or is activated. In such a control device, the period of time required for determining the activation of the sensor body is not excessively long as opposed to the conventional control device.

In the control device, after the activation determination unit determines that the sensor body is activated, the micro current supply unit resumes the supply of micro current to the oxygen concentration measuring cell, such that oxygen is supplied to the closed space of the electrode of the oxygen concentration measuring cell opposite to the other electrode defining the measurement gas chamber. As a result, the closed space is prevented from losing its function as an internal reference oxygen source because of the long discontinuation of the supply of micro current.

DETAILED DESCRIPTION OF PREFERRED EMBODIMENT

Figure 2:
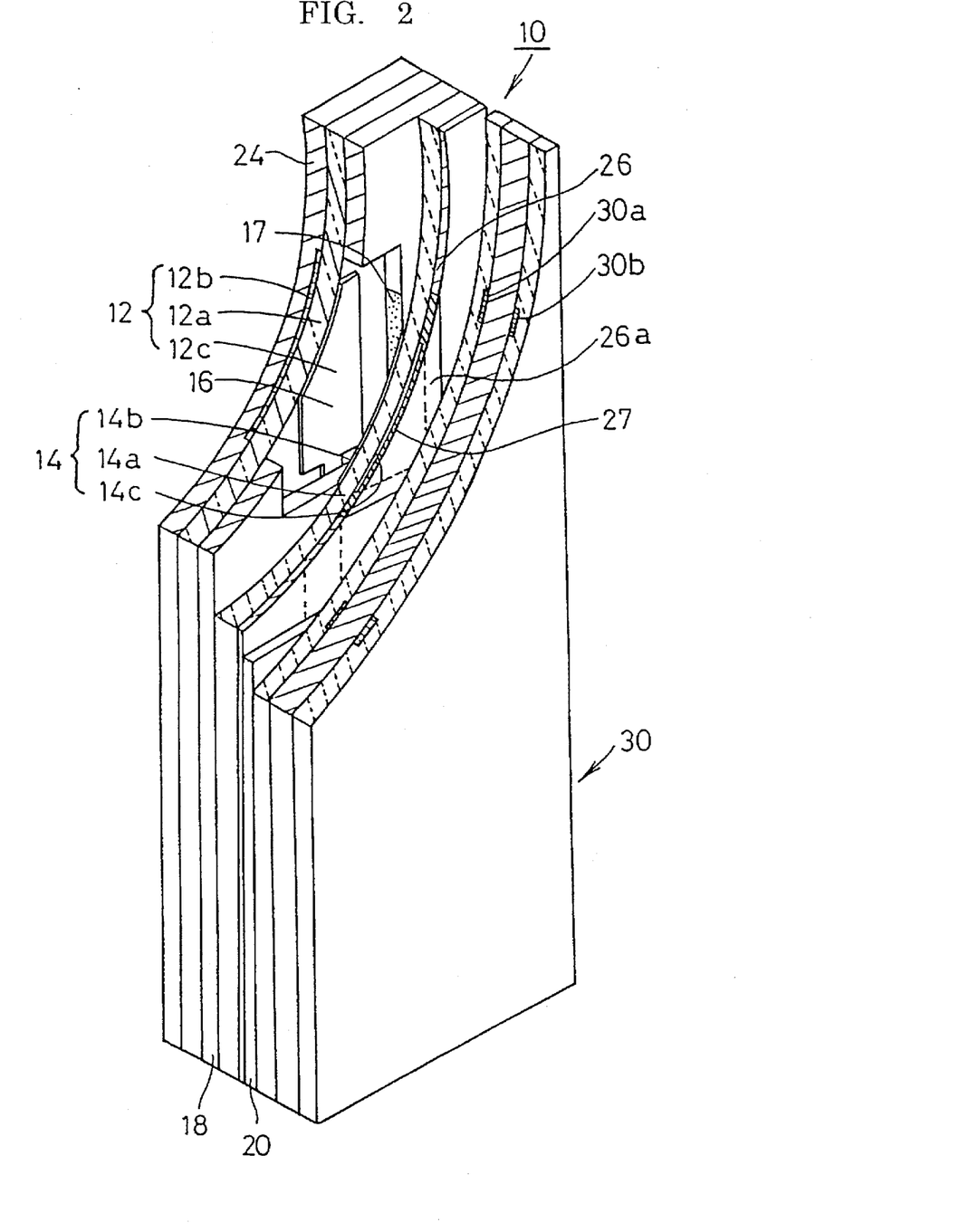
FIG. 2 is a partly broken perspective view of an air/fuel ratio sensor body of the embodiment.

In an embodiment according to the invention an air/fuel ratio sensor 10 is attached to an exhaust pipe of an engine for detecting the air/fuel ratio of the fuel mixed air supplied to the engine, from the concentration of the oxygen in the exhaust gas from the engine. As shown in FIG. 2, the air/fuel ratio sensor 10 is composed of a sensor body provided with an oxygen concentration measurement cell or battery element 12, an oxygen pumping cell or pump element 14 and a spacer 18. The battery element 12 has porous electrodes 12b and 12c formed on both sides of a planar solid electrolytic layer 12a. The pump element 14 has porous electrodes 14b and 14c formed on both sides of a planar solid electrolytic layer 14a. The spacer 18 is provided between the elements 12 and 14 to define a measurement gas chamber 16. A heater 30 for heating the elements 12 and 14 is attached via a spacer 20 at a predetermined interval from the pump element 14.

The battery element 12 is made by forming the pair of porous electrodes 12b and 12c on both side faces of the solid electrolytic layer 12a. In the same manner the pump element 14 is made by forming the pair of porous electrodes 14b and 14c on both side faces of the solid electrolytic layer 14a. The porous electrodes 12b, 12c, 14b and 14c are each formed of a base of yttria-zirconia solid solution and a remainder of platinum.

The solid electrolytic layers 12a and 14a can be formed of yttria-zirconia or calcia-zirconia solid solution, as known. Furthermore, the solid solution can be either cerium dioxide, thorium dioxide, hafnium dioxide, perovskite, trivalent metal oxide, or other can be used.

The pump element 14 is covered with an insulating layer 26 of alumina having a cavity 26a corresponding to the porous electrode 14c. A porous electrode protective layer 27 mainly of alumina is disposed in the cavity 26a for covering or protecting the porous electrode 14c.

The measurement gas chamber 16 is defined by the spacer 18 having recesses corresponding to the porous electrodes 12c and 14b, between the battery element 12 and the pump element 14. The porous electrodes 12c and 14b are thus exposed in the measurement gas chamber 16. The spacer 18 is formed of alumina, spine 1, forsterite, steatite, zirconia or other, as is known.

The spacer 18 has a plurality of pores for connecting the measurement gas chamber 16 to the outside. A diffusion controlled layer 17 is formed by filling porous filler of alumina in the pores, for example, such that the rate of the flow of measurement gas into the measurement gas chamber 16 is determined.

Figure 1:
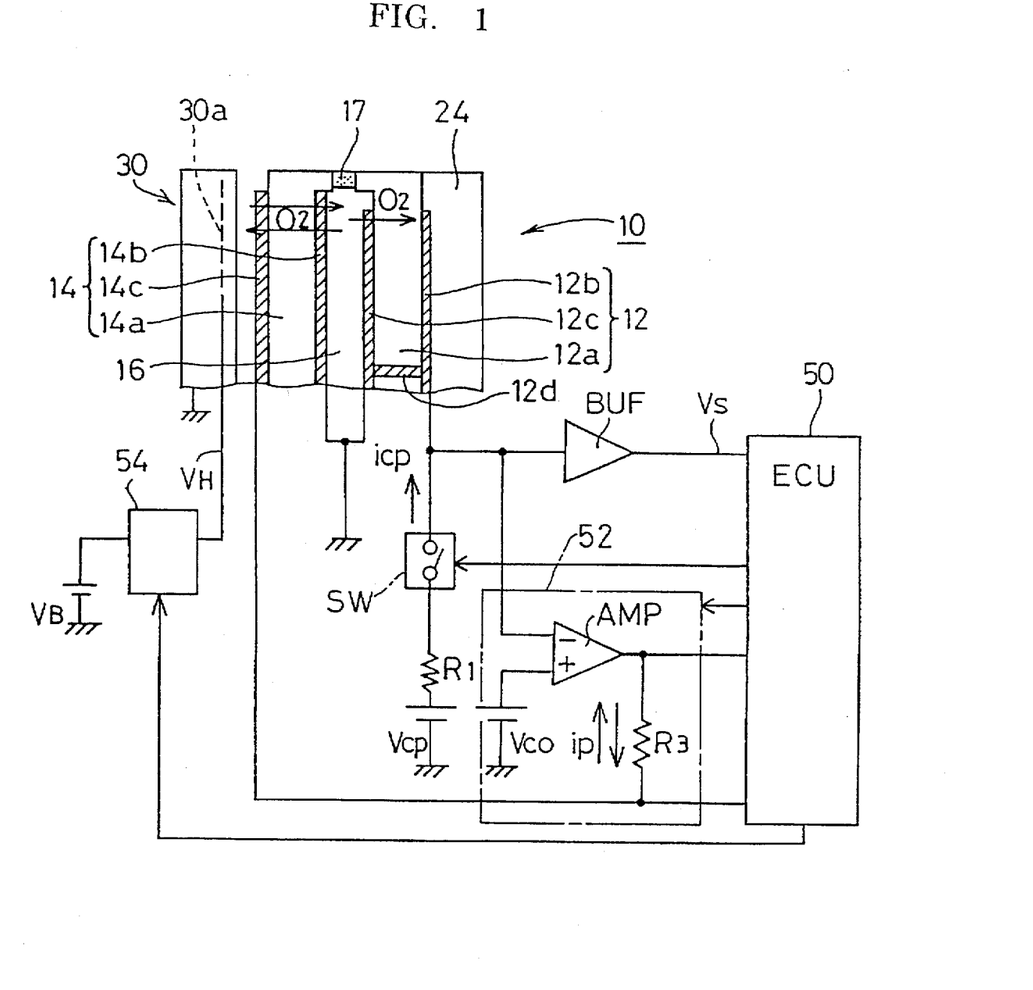
FIG. 1 is a diagrammatic representation of an air/fuel ratio sensor system embodying the present invention.

As shown in FIG. 2, a shield 24 formed of a solid electrolyte is attached to the exterior of the battery element 12, covering the porous electrode 12b. When a micro current icp is supplied from the porous electrode 12b toward the porous electrode 12c of the battery element 12 by a detection circuit 52 described later, the porous electrode 12b forms a closed space and the oxygen pumped into the closed space is kept inside. As shown in FIG. 1, the battery element 12 is provided with a leakage resistor 12d for letting part of oxygen leak from the porous electrode 12b to the measurement gas chamber 16. When the micro current icp is supplied by the detection circuit 52, the concentration of the oxygen in the porous electrode 12b becomes constant, and an electromotive force is generated in the battery element 12 corresponding to the concentration of the oxygen in the measurement gas chamber 16. In this case the constant oxygen concentration in the porous electrode 12b is a reference concentration.

As shown in FIG. 2, an exothermic pattern 30a is formed on one side of the heater 30 opposite to the pump element 14, while a known migration preventive pattern 30b is formed on the other side of the heater 30.

The structure of a system for controlling the air/fuel ratio sensor 10 and determining the activation of the elements 12 and 14 is now explained referring to FIG. 1.

As shown in FIG. 1, the porous electrodes 12c and 14b defining the measurement gas chamber 16 therebetween are grounded. The outer porous electrodes 12b of the battery element 12 and 14c of the pump element 14 are connected to the detection circuit 52 for controlling a pump current, respectively. The porous electrode 12b closed by the shield 24 is connected via an analog or other switch SW to one end of a resistor R1 with a constant voltage Vcp applied to the other end thereof. The resistor R1 supplies a substantially constant micro current icp to the battery element 12 and has a remarkably larger resistance as compared with the internal resistance of the battery element 12.

The porous electrode 12b of the battery element 12 is connected to a minus input terminal of a differential amplifier AMP in the detection circuit 52, and a reference voltage Vco is supplied to a plus input terminal of the differential amplifier AMP. The differential amplifier AMP, therefore, transmits the voltage corresponding to a difference between the reference voltage Vco and an interelectrode voltage Vs of battery element 12, via a resistor R3 to the porous electrode 14c of the pump element 14 facing the heater 30. As a result, a bidirectional pump current ip flows to and from the pump element 14 corresponding to the voltage transmitted from the differential amplifier AMP.

In the embodiment, when the switch SW is turned on, the micro current icp is transmitted to the battery element 12 and oxygen is pumped into the porous electrode 12b. The porous electrode 12b serves as an internal reference oxygen source, and the interelectrode voltage Vs is generated between the porous electrodes 12b and 12c of the battery element 12, corresponding to the concentration of oxygen in the measurement gas chamber 16 and the reference oxygen concentration of the porous electrode 12b. Furthermore, when the detection circuit 52 is operated, the pump current ip is supplied from the differential amplifier AMP to the pump element 14, such that the interelectrode voltage Vs of the battery element 12 reaches the reference voltage Vco of, for example, 450 mV, and the concentration of the oxygen in the measurement gas chamber 16 remains constant.

The resulting pump current ip, which corresponds to the concentration of oxygen in the surrounding gas measurement atmosphere, is converted to a voltage signal via the resistor R3 in the detection circuit 52. The voltage signal, which represents the oxygen concentration of the exhaust gas from the engine and the air/fuel ratio, is transmitted to an electronic control unit or ECU50 composed of a microcomputer or other for controlling the engine.

In the embodiment the change-over condition of the switch SW and the pump current control executed in the detection circuit 52 are controlled by the ECU50.

The exothermic pattern 30a of the heater 30 is connected to a heater energizing circuit 54, which receives a battery voltage VB and transmits a heater voltage VH for energizing the heater 30. The battery element 12 is connected to a buffer circuit BUF for transmitting the interelectrode voltage Vs directly to the ECU50.

The heater energizing circuit 54 is operated by the ECU50 at the same time when the engine is started, the voltage VH is applied to the exothermic pattern 30a of the heater 30, and the battery element 12 and the pump element 14 are heated. The interelectrode voltage Vs of the battery element 12 transmitted from the buffer circuit BUF determines whether or not the battery element 12 and the pump element 14 are activated. Subsequently, the air/fuel ratio is detected by the air/fuel ratio sensor 10 and the air/fuel ratio of the engine starts to be controlled based on the detected air/fuel ratio.

Figure 3:
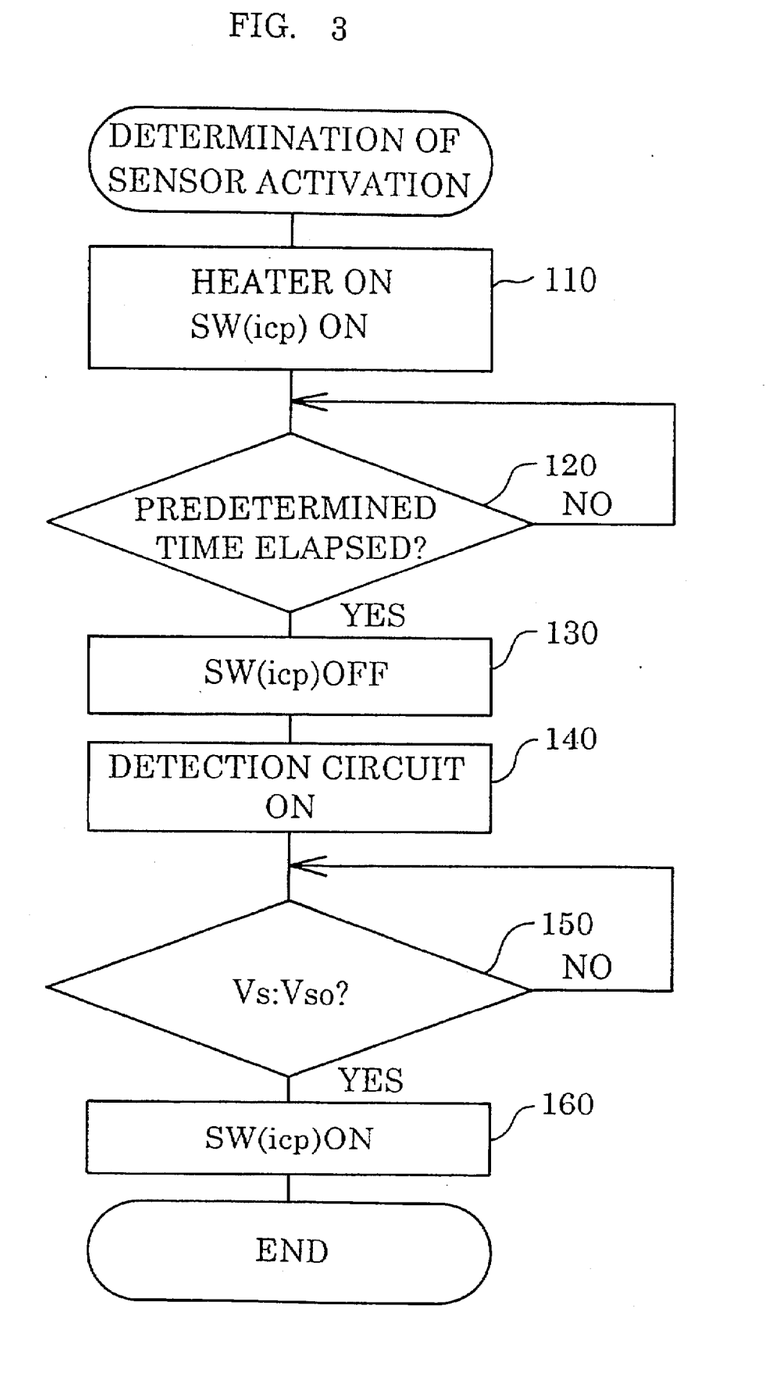
FIG. 3 is a flowchart showing the process of sensor activation determination executed in an ECU of the embodiment.

Although various control processes are carried out in the ECU50, the process steps for determining the activation of the air/fuel ratio sensor 10, according to the invention, are now explained referring to the flowchart of FIG. 3.

The sensor activation is determined immediately after the engine is started. When the process of determination is started, first at step 110, the heater energizing circuit 54 is operated turning on the heater 30 and the switch SW is turned on. The micro current iep is thus supplied to the battery element 12.

Subsequently, it is determined at step 120 whether or not a predetermined period of time ΔT of, for example, 5 seconds has elapsed after the micro current icp was supplied. If the answer to the step 120 is negative, it keeps timing until the predetermined period of time elapses. When the answer to the step 120 is affirmative, at step 130 the switch SW is turned off, thereby stopping the supply of the micro current iep to the battery element 12. Subsequently, at step 140 the detection circuit 52 is operated, and the pump current control is started. Specifically, the pump current ip is supplied from the difference amplifier AMP to the pump element 14.

Subsequently, it is determined at step 150 whether or not the interelectrode Vs of the battery element 12 transmitted from the buffer circuit BUF to the ECU50 is controlled to reach an activation determination voltage Vso (=Vco±α), which is predetermined according to the target reference voltage Vco. When the answer to the step 150 is negative, the pump current ip continues to be supplied under the control of the detection circuit 52 until the interelectrode voltage Vs of the battery element 12 reaches the reference voltage Vco.

After it is determined at step 150 that the interelectrode voltage Vs is controlled to reach the activation determination voltage Vso and the air/fuel ratio sensor 10 is activated, at step 160 the switch SW is turned on, resuming the supply of the micro current iep to the battery element 12, and the process once ends.

In the embodiment, after the sensor activation determination process ends, a known air/fuel ratio control process is started. Specifically, the voltage at both ends of the resistor R3 is transmitted from the detection circuit 52 to the ECU50 as a detection signal of air/fuel ratio. Subsequently, in the ECU50 the quantity of fuel supplied to the engine is controlled using the detection signal, such that the air/fuel ratio reaches the target air/fuel ratio.

Figure 4:
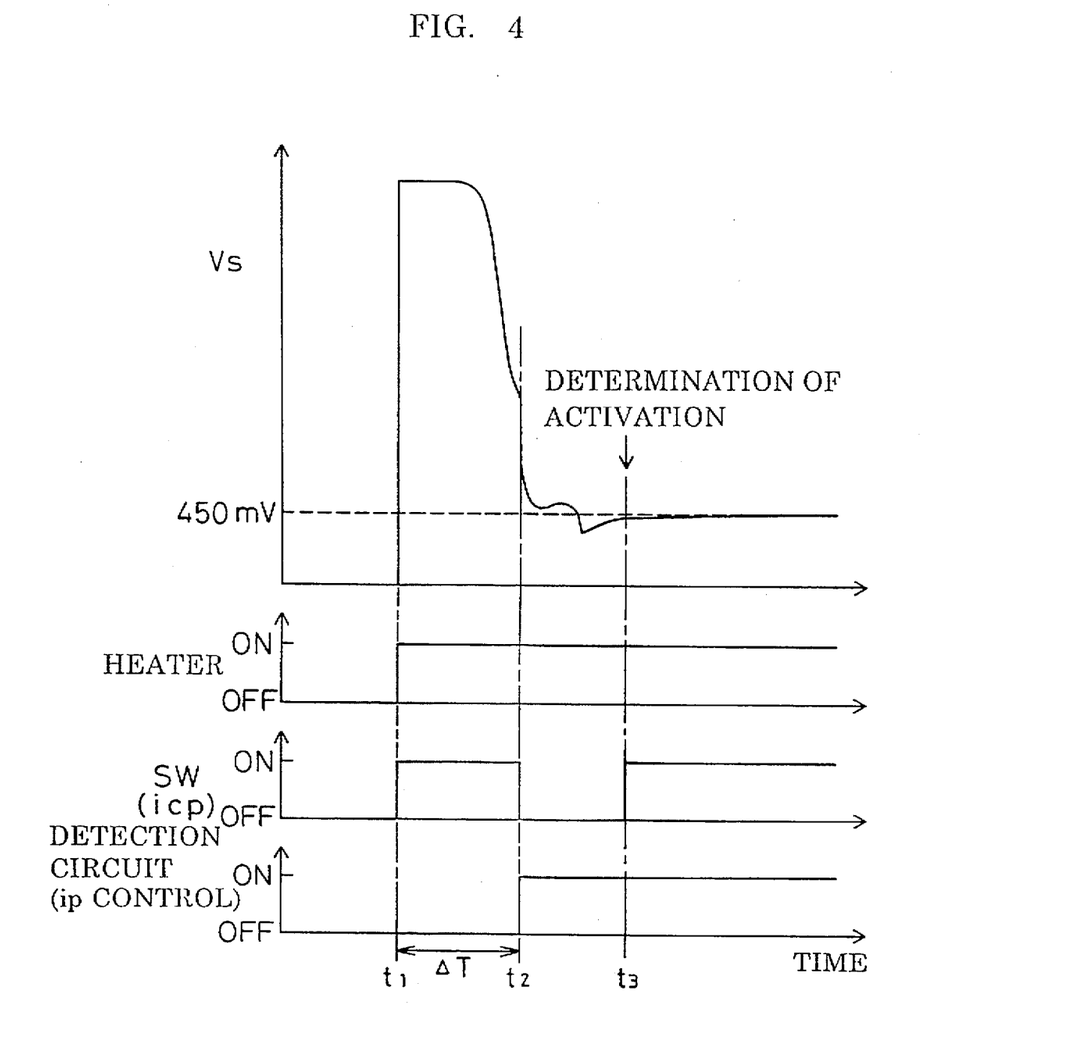
FIG. 4 is a time chart explaining the process of determining the activation of the sensor in the embodiment.

As aforementioned, in the embodiment, as shown in FIG. 4, at time t1 when the engine is started, the heater 30 is turned on to start heating the battery element 12 and the pump element 14. At the same time, the switch SW is turned on, the micro current iep is supplied to the battery element 12, and oxygen is pumped into the porous electrode 12b of the battery element 12. After the predetermined period of time ΔT, for example, 5 seconds has elapsed, at time t2 the supply of the micro current icp to the battery element 12 is stopped, and the detection circuit 52 is operated to start controlling the pump current ip.

When the pump current control is started, the closed space of the porous electrode 12b of the battery element 12 functions as the internal reference oxygen source, because the sufficient quantity of oxygen is pumped into the closed space by supplying the micro current iep to the porous electrode 12 b. Therefore, the interelectrode voltage Vs is generated between the porous electrodes 12b and 12c of the battery element 12, corresponding to the concentration of oxygen in the measurement gas chamber 16 without being affected by the internal resistance of the battery element 12. When the micro current icp is supplied to the battery element 12 immediately after the heater 30 turns on, the temperature of the battery element 12 is low while the internal resistance thereof is large. The interelectrode voltage Vs of the battery element 12 is increased by the voltage drop, i.e. the internal resistance multiplied by the micro current icp. In the embodiment, however, the detection circuit 52 starts controlling the pump current at the same time when the supply of the micro current icp to the battery element 12 is stopped. Therefore, after the time t2 when the pump current control is started, the interelectrode voltage Vs of the battery element 12 corresponds only to the concentration of oxygen in the measurement gas chamber 16 without being influenced by the internal resistance of the battery element 12.

Additionally, when the detection circuit 52 starts controlling the pump current, a voltage is generated, corresponding to the deviation between the interelectrode voltage Vs of the battery element 12 and the reference voltage Vco, and the pump current ip corresponding to the generated voltage is supplied to the pump element 14. The internal resistance of the pump element 14 is still large before the air/fuel ratio sensor 10 is activated. Therefore, the desired pump current ip cannot be supplied to the pump element 14 by the detection circuit 52, and the interelectrode voltage Vs of the battery element 12 cannot be adjusted to the reference voltage Vco. After the air/fuel ratio sensor 11 is sufficiently heated by the heater 30 and activated, the interelectrode voltage Vs of the battery element 12 can be adapted to the reference voltage Vco and the oxygen concentration of the exhaust gas can be detected precisely.

Although the air/fuel ratio cannot be precisely detected from the pump current ip at this time, it can be determined whether the measurement gas is lean or rich. The air/fuel ratio can be controlled with less precision in the control mode different from the usual control mode, when the air/fuel ratio sensor 10 is insufficiently activated. If the air/fuel ratio is controlled beforehand in the different mode, the usual control over the air/fuel ratio can be started earlier.

In the embodiment after the pump current begins to be controlled by the detection circuit 52, the interelectrode voltage Vs of the battery element 12 is monitored until the interelectrode voltage Vs is controlled to reach the target voltage or reference voltage Vco of 450 mV, for example. At the time t3 when the interelectrode voltage Vs reaches the reference voltage Vco, it is determined that the air/fuel ratio sensor 10 is ready to precisely detect the oxygen concentration in the exhaust gas, and the process goes to the usual air/fuel ratio control phase.

Consequently, in the embodiment, after the heater 30 is energized, the air/fuel ratio sensor 10 can be activated earlier as compared with in the conventional method. Additionally, the period of time from when the engine is started till the air/fuel ratio control is started can be shortened. Therefore, the purification of the exhaust gas from the engine by means of the air/fuel ratio control can be promoted and the discharge of toxic components to the air can be prohibited.

This invention has been described above with reference to the preferred embodiment as shown in the figures. Modifications and alterations may become apparent to one skilled in the art upon reading and understanding the specification. Despite the use of embodiments for illustration purposes, the invention is intended to include all such modifications and alterations within the spirit and scope of the appended claims.

For example, in the embodiment during the sensor activation determination process, the micro current icp is supplied to the battery element at the same time when the heater 30 is energized. After the predetermined period of time ΔT elapses, the supply of the micro current icp is stopped, until it is determined that the air/fuel ratio sensor 10 is activated. However, if the oxygen in the closed space of the porous electrode 12b of the battery element 12 partly leaks to the measurement gas chamber 16, the reference oxygen concentration cannot be maintained in the closed space after the supply of the micro current icp is stopped until the sensor activation. In this case, the control over the pump current can be periodically halted while the micro current icp is supplied to the battery element 12, between the time t2 and t3, i.e. from when the pump current control is started until the sensor activation. In this alternative method, the reference oxygen concentration can be maintained in the closed space formed by the porous electrode 12b of the battery element 12, the pump current can be precisely controlled, and, additionally, it can be precisely determined that the air/fuel ratio sensor is activated.

What is claimed is:

1. A method of controlling an air/fuel ratio sensor, where said air/fuel ratio sensor comprises:

a sensor body comprising an oxygen pumping cell and an oxygen concentration measuring cell, said oxygen pumping cell and said oxygen concentration measuring cell being each formed of a solid electrolytic layer conductive of oxygen ion interposed between a first porous electrode and a second porous electrode each disposed such that said first electrode of said oxygen pumping cell and first electrode of said oxygen concentration measuring cell define a measurement gas chamber communicating via a diffusion controlled layer to the gas to be measured and that said second electrode of said oxygen concentration measuring cell opposite to said measurement gas chamber forms a closed space, where part of the oxygen in said closed space being able to leak via a leakage resisting part to the outside;

a heater for heating and activating said sensor body;

a heater energizing means for energizing said heater and heating said air/fuel ratio sensor;

a micro current supply means for supplying a micro current to said oxygen concentration measuring cell so that the oxygen in said measurement gas chamber is pumped into said closed space and causing said closed space to function as an internal reference oxygen source;

a measurement means for measuring the interelectrode voltage of said oxygen concentration measuring cell; and a pump current control means for supplying a pump current to said oxygen pumping cell, said air/fuel ratio sensor being able to detect the oxygen concentration of measurement gas from the pump current controlled by said pump current control means and the interelectrode voltage of said oxygen concentrations measuring cell measured by said measurement means, and said air/fuel ratio sensor being controlled such that said concentrations of oxygen can be detected instantly after said heater is turned on by said heater energizing means, said method comprising the steps of:

starting said heater energizing means, for energizing said heater while concurrently operating said micro current supply means to supply the micro current to said oxygen concentration measuring cell, causing said closed space to function as the internal reference oxygen source;

allowing a predetermined period of time to elapse while concurrently energizing said heater and supplying a micro current to said oxygen concentration measuring cell; and stopping said micro current supply means from supplying the micro current to said oxygen concentration measuring cell while at the same time starting said pump current control means for supplying a pump current to said oxygen pumping cell.

2. A method of controlling an air/fuel ratio sensor according to claim 1, further comprising:

after the pump current control is started, activating said sensor body when the interelectrode voltage of said oxygen concentrations measuring cell reaches a predetermined voltage by means of said pump current control.

3. A method of controlling an air/fuel ratio sensor according to claim 2, further comprising the steps of:

determining that said sensor body is activated; and, restarting said micro current supply means for supplying the micro current to said oxygen concentration measuring cell while said sensor body is activated.

4. A method of controlling an air/fuel ratio sensor according to claim 2, further comprising periodically supplying the micro current to the oxygen concentration measuring cell while the pump current supply is halted, between the time when the pump current control is started until the sensor body is activated.

5. A control device for controlling an air/fuel ratio sensor, said air/fuel ratio sensor comprising:

a sensor body comprising an oxygen pumping cell and an oxygen concentration measuring cell, said oxygen pumping cell and said oxygen concentration measuring cell being each formed of a solid electrolytic layer conductive of oxygen ion interposed between a first porous electrode and a second porous electrode each disposed such that said first electrode of said oxygen pumping cell and said first electrode of said oxygen concentration measuring cell define a measurement gas chamber communicating via a diffusion controlled layer to the gas to be measured and that said second electrode of said oxygen concentration measuring cell opposite to said measurement gas chamber forms a closed space, where part of the oxygen in said closed space being able to leak via a leakage resisting part to the outside;

a heater for heating and activating, said sensor body;

a heater energizing means for energizing said heater and heating said air/fuel ratio sensor;

a micro current supply means for supplying a micro current to said oxygen concentration measuring cell so that the oxygen in said measurement gas chamber is pumped into said closed space and causing said closed space to function as an internal reference oxygen source;

a measurement means for measuring the interelectrode voltage of said oxygen concentration measuring cell; and a pump current control means for supplying a pump current to said oxygen pumping cell, said air/fuel ratio sensor being able to detect the concentration of oxygen in the gas to be measured from the pump current controlled by said pump current control means and the interelectrode voltage of said oxygen concentration measuring cell measured by said measurement means, and said air/fuel ratio sensor being controlled such that said concentration of oxygen can be detected instantly after said heater is turned on by said heater energizing means, said control device comprising:

a micro current supply start means for starting said heater energizing means energizing said heater while at the same time operating said micro current supply means;

a timer means for causing said micro current supply start means to operate said micro current supply means concurrently with said heater energizing means for a predetermined period of time; and a supply stop means responsive to said timer means for stopping said micro current supply means from supplying the micro current to said oxygen concentration measuring cell after the micro current is supplied for the predetermined period of time; and a pump current control start means for starting said pump current control means for controlling the pump current at the same time that the supply of the micro current is stopped by said supply stop means.

6. A control device for controlling an air/fuel ratio sensor according to claim 5, further comprising an activation determination means for monitoring whether the interelectrode voltage of said oxygen concentration measuring cell has reached a predetermined voltage as a result of controlling the pump current when said pump current control start means starts said pump current control means controlling the pump current, and means for activating said sensor body in response to said activation determination means when said interelectrode voltage reaches said predetermined voltage.

7. A control device of controlling an air/fuel ratio sensor according to claim 6, further comprising a micro current supply restart means for restarting said micro current supply means when said activation determination means determines that said sensor body is activated.

8. A control device for controlling an air/fuel ratio sensor according to claim 6, further comprising means for periodically supplying the micro current to the oxygen concentration measuring cell while the pump current supply is halted, between the time when the pump current control is started until the sensor body is activated.

* * * * *